United States Patent [19]

Ohlendorf et al.

[11] Patent Number: 4,831,167
[45] Date of Patent: May 16, 1989

[54] PROCESS FOR DIASTEREOSELECTIVE REDUCTION OF 3-AMINO-1-BENZOXEPIN-5(2H)-ONES

[75] Inventors: Heinrich W. Ohlendorf, Garbsen; Uwe Maetzel, Burgdorf, both of Fed. Rep. of Germany

[73] Assignee: Kali-Chemie Pharma GmbH, Hanover, Fed. Rep. of Germany

[21] Appl. No.: 110,560

[22] Filed: Oct. 20, 1987

Related U.S. Application Data

[63] Continuation of Ser. No. 794,760, Nov. 4, 1985, abandoned.

[30] Foreign Application Priority Data

Nov. 5, 1984 [DE] Fed. Rep. of Germany ....... 3440295

[51] Int. Cl.$^4$ .................................... C07D 313/08
[52] U.S. Cl. ............................................. 549/355
[58] Field of Search ...................................... 549/355

[56] References Cited

U.S. PATENT DOCUMENTS 4,279,904 7/1981 Ohlendorf et al. .
4,279,905 7/1981 Ohlendorf et al. ................. 549/350

OTHER PUBLICATIONS

S. Mitsui et al, Tetrahedron, vol. 29 (1973), pp. 1531–1539.
M. J. F. Burman et al, Tetrahedron Letters, No. 18 (1976), pp. 1535–1538.
David C. Horwell et al, Chemical Abstracts 90:168189a (1979).
F. Van Rantwijk et al, Chemical Abstracts 95:61284d (1981).

Baker, et al, "The Reduction of Amide Vinylogs", J. Am. Chem. Soc., 68:2009–11 (1946).
Kochetkov, "Beta-Aminovinyl Ketones II", Chem. Abstracts, 49:6090i (1955).
Bowden, et al, "Researches on Acetylenic Compounds. Part II", J. Chem. Soc., (1946), pp. 45–52.
Horwell, et al, "Stereoselectivity in the Catalytic Hydrogenation of an Enamine.", Synthetic Communications, 9(3):223–31 (1979).
Martin, et al, "Ketones VIII. Some Reactions of 1-(-Dimethylamino)-4-methyl-1-penten-3-one", J. Org. Chem., 31:943–6 (1966).
Greenhill, et al, "Reduction of Enaminones in the Preparation of 3-Aminocyclohexanols", J. C. S. Perkin I., pp. 588–591 (1975).
Greenhill, "Enaminones", Chem. Soc. Reviews, 6:277–95 (1977).
Phillips et al., Jour. Amer. Chem. Soc., vol. 78, pp. 140–145 (1956).
Albertson, Jour. Amer. Chem. Soc., vol. 74, pp. 249–251 (1952).

Primary Examiner—Richard L. Raymond
Attorney, Agent, or Firm—Foley & Lardner, Schwartz, Jeffery, Schwaab, Mack, Blumenthal & Evans

[57] ABSTRACT

A process for producing cis-2,3,4,5-tetrahydro-3-amino-1-benzoxepin-5-ols in which 3-amino-1-benzoxepin-5(2H)-ones are diastereoselectively reduced in a single stage by catalytic hydrogenation in the presence of a platinum oxide catalyst and an equivalent amount of an acid in a polar protic solvent, or by reaction with a borane/amine complex in an aprotic solvent, optionally in the presence of an added lower aliphatic carboxylic acid.

10 Claims, No Drawings

PROCESS FOR DIASTEREOSELECTIVE REDUCTION OF 3-AMINO-1-BENZOXEPIN-5(2H)-ONES

This application is a continuation of application Ser. No. 794,760, filed Nov. 4, 1985 now abandoned.

BACKGROUND OF THE INVENTION

The present invention relates to a process for diastereoselective reduction of 3-amino-1-benzoxepin-5(2H)-ones to 2,3,4,5-tetrahydro-3-amino-1-benzoxepin-5-ols in which the substituents in the 3- and 5-positions are predominantly cis to each other.

2,3,4,5-tetrahydro-3-amino-1-benzoxepin-5-ols and their acid addition salts are known from U.S. Pat. No. 4,279,904. These compounds have two asymmetric centers (C3 and C5, Cf. the following formula I) on which substituents in any given case may be arranged in the R- or the S-configuration, so that these substances occur in several stereoisomeric forms. These substances exhibit a pharmacological activity which has a favorable effect on gastrointestinal motility and are therefore useful as pharmaceuticals. In this respect cis-2,3,4,5-tetrahydro-3-amino-1-benzoxepin-5-ols, in which the substituents in the 3- and 5-positions are cis to each other, have proven to be especially suitable for oral application.

In accordance with the process described in U.S. Pat. No. 4,279,904, 2,3,4,5-tetrahydro-3-amino-1-benzoxepin-5-ols can be produced from the corresponding 3-amino-1-benzoxepin-5(2H)-ones by one stage or two stage reduction by treatment with specific hydride reducing agents and/or by catalytic hydrogenation in the presence of Raney nickel.

The single stage reduction is achieved with sodium borohydride in a neutral to weakly acid medium or with sodium cyanoborohydride in an acid medium or by catalytic hydrogenation in the presence of Raney nickel in a protic solvent. In these procedures mixtures of the different diastereoisomers are formed.

From such mixtures the racemate having the cis configuration or the racemate having the trans configuration must first be enriched and then finally isolated by means of expensive separating processes, e.g. fractional crystallization of suitable salts or chromatographic processes. The resulting racemic cis-2,3,4,5-tetrahydro-3-amino-1-benzoxepin-5-ol, which is substantially free of trans epimers, or the corresponding racemate with the trans configuration, which is substantially free of cis epimers, can subsequently be separated in a known manner into its optical isomers if desired.

In the two stage reduction process described in U.S. Pat. No. 4,279,904, the 3-amino-1-benzoxepin-5(2H)-one is first converted by hydrogenation of the 3,4-double bond into the corresponding 3-amino-3,4-dihydro-1-benzoxepin-5(2H)-one. This reaction may be achieved by catalytic hydrogenation in the presence of Raney-nickel in an aprotic solvent or by reaction with sodium cyanoborohydride in a weakly acid medium. The 5-keto group is then reduced in a second reduction stage to a hydroxy group. This reaction may be effected using the hydride reducing agents listed in U.S. Pat. No. 4,279,904. Only in this two stage reduction process is it possible to achieve in the second reduction stage an enrichment of cis-2,3,4,5-tetrahydro-3-amino-1-benzoxepin-5-ols in the reduction product by using a special selective hydride reducing agent which, however, is technically very expensive to work with.

SUMMARY OF THE INVENTION

It is the object of the present invention to provide an improved process for diastereoselectively producing cis-2,3,4,5-tetrahydro-3-amino-1-benzoxepin-5-ols.

This and other objects of the invention are achieved by providing a process for producing cis-2,3,4,5-tetrahydro-3-amino-1-benzoxepin-5-ols corresponding to the Formula I:

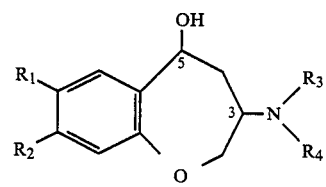

wherein
the substituents in the 3- and 5-positions are cis to each other, and
$R_1$ represents hydrogen, halogen, or alkyl having 1-4 carbon atoms,
$R_2$ represents hydrogen, halogen, or alkyl having 1-4 carbon atoms,
$R_3$ represents hydrogen or alkyl having 1-5 carbon atoms, and
$R_4$ represents hydrogen and alkyl having 1-5 carbon atoms, and their acid addition salts, wherein
a 3-amino-1-benzoxepin-5(2H)-one corresponding to the Formula II

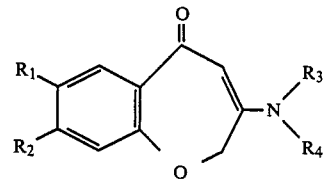

wherein
$R_1$, $R_2$, $R_3$ and $R_4$ have the above meanings is diastereoselectively reduced to a mixture of 2,3,4,5-tetrahydro-3-amino-1-benzoxepin-5-ols containing a predominant portion of cis-compounds corresponding to Formula I by (a) reacting a compound corresponding to Formula II with a borane/amine complex in an aprotic organic solvent containing 0-50 volume percent of a liquid, lower aliphatic carboxylic acid, or (b) reducing a compound corresponding to Formula IIa

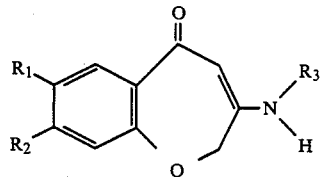

wherein
$R_1$, $R_2$ and $R_3$ have the above meanings, with hydrogen in the presence of a platinum oxide catalyst in a protic, polar, organic solvent in the presence of an equivalent amount of an acid which is stable under the reaction conditions, and isolating the cis-2,3,4,5-tetrahydro-3-amino-1-benzoxepin-5-ol from the resulting reaction product.

DETAILED DESCRIPTION OF THE INVENTION

A process has now been found by means of which a diastereoselective reduction of 3-amino-1-benzoxepin-5(2H)-ones can be achieved in a single reaction stage in good yields and with high diastereoselectivity for 2,3,4,5-tetrahydro-3-amino-1-benzoxepin-5-ols having predominantly the cis configuration.

The invention is a process for producing cis-2,3,4,5-tetrahydro-3-amino-1-benzoxepin-5-ols corresponding to the general formula I

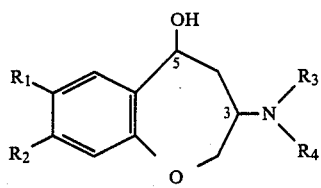

wherein
the substituents in the 3- and 5-positions are cis to each other, and
$R_1$ represents hydrogen, halogen or alkyl having 1–4 carbon atoms;
$R_2$ represents hydrogen, halogen or alkyl having 1–4 carbon atoms;
$R_3$ represents hydrogen or alkyl having 1–5 carbon atoms, and
$R_4$ represents hydrogen or alkyl having 1–5 carbon atoms,
and their acid additions salts, wherein
a 3-amino-1-benzoxepin-5(2H)-one corresponding to the general formula II

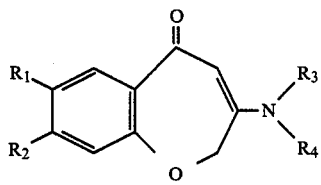

wherein
$R_1$, $R_2$, $R_3$ and $R_4$ have the above meanings is diastereoselectively reduced to a mixture of 2,3,4,5-tetrahydro-3-amino-1-benzoxepin-5-ols containing a predominant proportion of cis compounds corresponding to Formula I by
(a) reacting a compound corresponding to Formula II with a borane/amine complex in an aprotic organic solvent containing 0–50 volume percent of a liquid, lower aliphatic carboxylic acid, or
(b) hydrogenating a compound corresponding to the general formula IIa

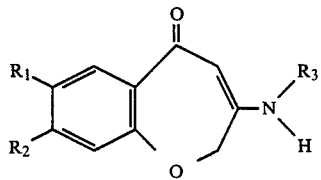

wherein
$R_1$, $R_2$ and $R_3$ have the above meanings with hydrogen in the presence of a platinum oxide catalyst in a polar, organic, protic solvent and in the presence of an equivalent amount of an acid which is stable under the conditions of the reaction,
and isolating the cis-2,3,4,5-tetrahydro-3-amino-1-benzoxepin-5-ol from the resulting reaction mixture in the form of its acid addition salt or its free base. If desired, the acid addition salt can be converted to the free base, or the free base can be converted to an acid addition salt.

According to procedure (a) of the process of the invention, the 3-amino-1-benzoxepin-5(2H)-one of Formula II is reduced by reaction with a borane/amine complex in which borane is bound to an amine component. Compounds of Formula II in which $R_1$ or $R_2$ represents halogen are preferred to be reduced according to this procedure. As the amine component of the borane/amine complex, those amines which are easily separated from the reaction mixture or from the resulting, basicly reacting compounds of Formula I are particularly suitable. Thus, for example, amines which are sufficiently volatile so that they can be removed by distillation or simple evaporation are suitable. Suitable amines include, for example, amines corresponding to the Formula III

wherein
$R_5$ represents hydrogen, methyl or ethyl, $R_6$ represents hydrogen, methyl or ethyl, and $R_7$ represents hydrogen, straight chain or branched lower alkyl, preferably with up to 4 carbon atoms, or if $R_5$ and $R_6$ are hydrogen, $R_7$ may represent phenyl or phenyl substituted with lower alkyl. In particular, aliphatic amines of Formula III, preferably primary or secondary amines, i.e. amines in which $R_5$ and/or $R_6$ represent hydrogen and $R_7$ represents straight chain or branched alkyl, are especially suitable. Examples of suitable amines include tert.-butylamine, diethylamine, or di- or trimethyl amine. Further, cyclic amines, such as pyridine, morpholine or N-lower alkylmorpholine, are suitable. The borane/tert.-butylamine complex has proven to be particularly advantageous.

Generally, at least equimolar amounts of the borane/amine complex are utilized. For example, amounts of from 2 to 3 moles of borane/amine complex per mole of compound of Formula II have proven to be effective.

Suitable solvents include aprotic, non-polar, organic solvents which are stable under the reaction conditions, preferably those solvents which are miscible with liquid lower aliphatic carboxylic acids or mixtures of such non-polar solvents with lower aliphatic carboxylic acids. Aromatic hydrocarbons, such as toluene or benzene, or halogenated hydrocarbons, such as methylene chloride, are particularly suitable as non-polar aprotic solvents. Suitable lower aliphatic carboxylic acids are liquid, lower alkyl carboxylic acids which are stable under the reaction conditions, for example alkane carboxylic acids having 2–4, preferably 2–3, carbon atoms, and particularly acetic acid.

The solvent may contain up to 50 volume percent of the aliphatic carboxylic acid. For example, solvent mixtures are suitable in which the volume relationship of non-polar solvent to lower carboxylic acid is between 9:1 and 1:1, preferably between 3:1 and 1:1, and particularly approximately 2:1. A solvent mixture which contains toluene and acetic acid in a volume relationship of 1.5-2.5:1 has proven to be particularly suitable.

The reaction temperature may lie between ambient temperature and approximately 100 degrees C. and may vary depending on the amount of acid in the reaction mixture. Thus, with a ratio of non-polar solvent to aliphatic carboxylic acid of from 3:1 to 1:1, temperatures between 30 and 80 degrees C., particularly 40 to 60 degrees C., have proven suitable, while at lower acid contents or in acid-free solutions, higher temperatures, for example temperatures between 60 and 100 degrees C., particularly 80 and 100 degrees C., are more advantageous. The reaction time varies depending on the reaction conditions which are used and may lie, for example, between approximately 2 and 75 hours.

In contrast to the reduction reactions known from U.S. Pat. No. 4,279,904 with the hydride reducing agents listed therein, the reduction of compounds of Formula II according to the invention with borane/amine complexes leads unexpectedly and surprisingly in only one reaction stage to high yields of 2,3,4,5-tetrahydro-3-amino-1-benzoxepin-5-ols with a cis epimer content which is already so high that substantially trans epimer-free cis-2,3,4,5-tetrahydro-3-amino-1-benzoxepin-5-ols can be isolated therefrom with only a small effort and expense. The reduction reaction of the invention leads not only to substantially better yields of the desired cis epimer compounds of Formula I, but also has the additional advantage that the handling of the reducing agents which are used is technically much simpler than it is to work with the only one of the hydride reducing agents suggested in U.S. Pat. No. 4,279,904 with which an enrichment in the cis epimer content of the reaction product may be obtained in the second reaction stage.

The hydrogenation of compounds of Formula IIa according to procedure (b) with hydrogen using platinum oxide as a catalyst takes place in a protic, polar, organic solvent in the presence of an equivalent amount of acid. Suitable protic, polar, organic solvents include lower alcohols, for example, alcohols with 1 to 3 carbon atoms, particularly methanol. Advantageously, a practically water-free solvent will be used, i.e. the solvent should desirably contain not more than about 1 percent water, preferably less than 0.5 percent.

Suitable acids include inorganic or organic acids which are stable under the reaction conditions. Examples of useful inorganic acids include hydrogen halide acids such as hydrochloric acid, sulfuric acid or phosphoric acid. Examples of suitable organic acids include lower aliphatic mono- or dicarboxylic acids which are not reducible under the reaction conditions, particularly aliphatic carboxylic acids having up to 5 carbon atoms such as, for example, oxalic acid and aromatic acids, e.g. benzene sulfonic acids which optionally may be substituted in the benzene ring with lower alkyl or halogen such as, for example, p-toluene sulfonic acid. In order to achieve optimum results, it is important that the amount of acid be precisely measured so that only 1 equivalent of acid ±5 percent is present per mole of compound of Formula IIa in the reaction mixture.

If desired, the compounds of Formula IIa and the acids can be added separately to the reaction mixture. For this purpose, water-free, easily measurable inorganic or organic acids are particularly suitable, e.g. gaseous inorganic acids such as hydrogen halide acids, particularly hydrochloric acid, or solid organic acids such as, for example, oxalic acid or p-toluene sulfonic acid.

It is also possible to first produce an acid addition salt from the compound of Formula IIa and the acid, which salt contains one equivalent of acid, and to then use the acid addition salt in the reaction. Useful acids to form the salts include all acids which form crystalline salts, particularly hydrogen halide acids, sulfuric acid, phosphoric acid or benzene sulfonic acids which may optionally be substituted in the benzene ring.

The hydrogenation is advantageously carried out at elevated pressure, for example, a hydrogen pressure of 5-100 bar, preferably 25-75 bar, and particularly preferably 40-60 bar. Commercially available platinum oxide may be used as the catalyst which contains a platinum content of 79-85 percent and is known, for example, under the designation "Adams Catalyst." The amount of the catalyst may vary depending on the hydrogen pressure used. Advantageously, the quantity of the catalyst will amount to at least 2 g per mole of compound of Formula IIa. Amounts of, for example, 2-20 g, particularly 2-5 g, of platinum per mole of compound of Formula IIa are suitable. The reaction can be carried out at ambient temperature or at elevated temperature, for example elevated temperatures up to 80 degrees C., preferably at temperatures between 30 and 80 degrees C., and particularly at temperatures between 40 and 60 degrees C. The Reaction time varies depending on the hydrogen pressure, temperature and amount of catalyst which are used. It may, for example, lie between 2 and 5 hours.

The hydrogenation process according to the invention has the advantage compared to the previously known reduction process for producing compounds of Formula I that the 3-amino-1-benzoxepin-5(2H)-one of Formula IIa can be converted in only one reaction step into 2,3,4,5-tetrahydro-3-amino-1-benzoxepin-5-ol with a cis epimer content which is already so high that with little expense and effort substantially trans-epimer-free cis-2,3,4,5-tetrahydro-3-amino-1-benzoxepin-5-ol can be isolated therefrom.

The 3-amino-1-benzoxepin-5(2H)-ones of Formula IIa are vinylogous amides. It is therefore surprising that when the compounds of Formula IIa are hydrogenated according to the invention with a platinum oxide catalyst under the reaction conditions used in the invention, a reduction of the double bond of the compound of Formula IIa and a reduction of the keto group to a hydroxy group take place without splitting the molecule, and the cis-2,3,4,5-tetrahydro-3-amino-1-benzoxepin-5-ol of Formula I is obtained in good yield. It is known from research reported in the literature relating to the behavior of vinylogous amides, i.e. beta-aminovinylketones, that upon catalytic hydrogenation in the presence of various hydrogenation catalysts, including platinum oxide, the catalytic hydrogenation either leads only to a reduction of the double bond and the corresponding saturated amino ketones are obtained, or when the reaction proceeds further, reduction of the double bond and hydrogenolytic splitting of the molecule lead to amines and saturated ketones. See, for example, J. Amer. Chem. Soc., 68: 2009, 2010 (1946) or Chem. Abs. 49: 6090e (1955).

The reduction of the compounds of Formula II according to the process of the invention proceeds with good yields and high diastereoselectivity. Thus, total yields of 2,3,4,5-tetrahydro-3-amino-1-benzoxepin-5-ols between 80 and 95 percent are generally obtained. The ratio of cis to trans epimers in the resulting reduction product is at least 7:3. Generally, the cis epimer content in the mixture lies between about 70 and about 85 percent, particularly approximately 80 percent.

The cis epimers from the mixtures of 2,3,4,5-tetrahydro-3-amino-benzoxepin-5-ols obtained according to the reduction process of the invention can be enriched and isolated in a known manner. For example, the free base or the acid addition salt can be subjected to fractional crystallization in a suitable solvent, for example lower alcohols. Advantageously, the reaction mixture is first converted to the acid addition salt and the salt is crystallized from a lower alcohol. Maleic acid, hydrochloric acid and p-toluenesulfonic acid have proven to be particularly suitable for forming salts to be fractionally crystallized in order to enrich the cis epimer content. Alcohols with 1 to 4 carbon atoms, preferably isopropanol, can be used as the lower alcohol. Because the cis epimer content in the reduction product produced in the reduction process of the invention is already very high, racemic cis-compounds containing less than 5 percent of the corresponding trans epimer can be obtained by only one or two recrystallizations. If desired, the recovery of the cis epimer from the mixture can also be achieved by chromatographic separation in a known manner, for example on silica gel or on aluminum oxide. As the elution agent there may be used, for example, methylene chloride containing a portion of a lower alkyl alcohol, particularly methanol, and a lower mono- or dialkyl amine or ammonia, particularly an aqueous ammonia solution. The high content of cis epimer in the raw product also proves very advantageous in this case because fewer mixed fractions arise in the chromatographic separation and also because separating materials with a low separation capacity may be used.

The resulting racemic cis-2,3,4,5-tetrahydro-3-amino-1-benzoxepin-5-ols corresponding to Formula I may, if desired, be separated in a known manner into their optically active antipodes by reacting them with suitable optically active acids and subsequently fractionally crystallizing the resulting salts. Also if desired, the free bases may be recovered in a known manner from acid addition salts of compounds coresponding to Formula I, and the free bases may if desired be converted again into other acid addition salts with pharmacologically acceptable acids.

The invention will be illustrated in further detail by the following examples which, however, are not to be taken as limiting the scope of the invention.

EXAMPLE 1

3,5-cis-3-methylamino-2,3,4,5-tetrahydro-1-benzoxepin-5-ol (A) By introducing 10.7 g of gaseous hydrogen chloride into 900 ml of methanol, a methanolic acid solution was produced. 56.7 g of 3-methylamino-1-benzoxepin-5(2H)-one were dissolved in this solution at room temperature while atmospheric moisture was excluded. The solution was combined with a suspension of 0.75 g platinum oxide catalyst (Adams Catalyst, platinum content 82 percent) in methanol. The reaction mixture was warmed to 50 degrees C. in an autoclave and purged with nitrogen. Thereafter hydrogenation was caried out at this temperature and under a hydrogen pressure of 50 bar for 2.5 hours with stirring by a stroke stirrer. After completion of the hydrogenation, the hydrogen was released and the mixture was purged with nitrogen and filtered. The filtrate solution was evaporated under vacuum. 68.5 g of hydrogenation product was obtained as a residue, which was a raw mixture of the hydrochlorides of 3,5-cis- and 3,5-trans-3-methylamino-2,3,4,5-tetrahydro-1-benzoxepin-5-ol.

The hydrogenation mixture which was obtained was analyzed by high performance liquid chromatography (HPLC). In the analysis the test sample was separated on silica gel (reversed phase material, Nucleosil-RP18-0.005 mm, produced by Machery and Nagel) and detected by UV-spectrometry (lamda=215 nm). The elution agent was a solvent mixture with a linear gradient comprising a water/phosphoric acid mixture (100/1) and a water/acetonitrile/phosphoric acid mixture (100/900/1). The content of the individual components in the analyzed hydrochloride mixture was determined by evaluation according to the surface percent method. The analysis showed that the mixture contained 76.8 percent hydrochloride of 3,5-cis-3-methylamino-2,3,4,5-tetrahydro-1-benzoxepin-5-ol and 18.6 percent hydrochloride of 3,5-trans-3-methylamino-2,3,4,5-tetrahydro-1-benzoxepin-5-ol.

(B) Isolation of the cis epimers:

The 3,5-cis-3-methylamino-2,3,4,5-tetrahydro-1-benzoxepin-5-ol from the mixture obtained in Example 1A could be isolated according to the following methods:

(B1) 29 g of the hydrochloride mixture obtained according to Example 1A were dissolved in 50 ml of isopropanol, and the solution was reduced in volume until the onset of crystallization and cooled. After cooling, the crystals which formed were removed by filtration, and the recrystallization was repeated once more. 20 g of 3,5-cis-3-methylamino-2,3,4,5-tetrahydro-1-benzoxepin-5-ol were obtained, melting point 190 degrees C.

(B2) 33 g of the hydrochloride mixture obtained according to Example 1A were reacted with 110 ml of concentrated aqueous ammonia solution in order to release the corresponding mixture of free bases, and the reaction mixture was extracted with methylene chloride. The methylene chloride phase was dried over sodium sulfate, and the solvent was evaporated. 28 g of the base mixture were obtained as a residue.

This mixture was dissolved in 130 ml isopropanol; the solution was combined with a hot solution of 20 g maleic acid in 60 ml isopropanol, and the resulting mixture was reduced in volume until the onset of crystallization. After the mixture had cooled, the crystallized maleate salt was removed by filtration and recrystallized from 450 ml isopropanol, melting point 148-150 degrees C.

To obtain the free base, the maleate salt of the title compound obtained as described above was reacted with concentrated aqueous ammonia solution, and the title compound which was released was extracted with methylene chloride. After drying of the methylene chloride phase and evaporation of the solvent, 21 g of 3,5-cis-3-methylamino-2,3,4,5-benzoxepin-5-ol were obtained, melting point 100-103 degrees C.

To convert the title compound into its hydrochloride, 19.3 g of the compound obtained as described above were dissolved in isopropanol, and the solution was reacted with 3.7 g gaseous hydrogen chloride. Subsequently, the solution was reduced in volume and cooled until the onset of crystallization. The resulting hydrochloride of the title compound was removed by filtration. Melting point 190 degrees C.

(B3) The free base mixture was obtained as described in Example 1B2 from the hydrochloride mixture obtained according to Example 1A. 4 g of the base mixture obtained in this way were subjected to chromatography on a chromatographic column containing 110 g silica gel (Lichroprep ® Si 60, available from Merck & Co.) under a pressure of approximately 2 bar utilizing a 100/20/2 mixture of methylenechloride/methanol/25 percent aqueous ammonia as the elution agent. After evaporation of the eluate, 2.9 g 3,5-cis-3-methylamino-2,3,4,5-tetrahydro-1-benzoxepin-5-ol were obtained having a melting point of 100–103 degrees C.

EXAMPLE 2

3,5-cis-3-methylamino-2,3,4,5-tetrahydro-1-benzoxepin-5-ol (A) 56.7 g 3-methylamino-1-benzoxepin-5(2H)-one and 57.1 g p-toluenesulfonic acid monohydrate were dissolved in 900 ml methanol. After addition of 0.75 g platinum oxide catalyst (Adams Catalyst), the reaction mixture was hydrogenated and worked up as described in Example 1A. 110 g of a raw mixture of the p-toluenesulfonic acid salts of 3,5-cis- and 3,5-trans-3-methylamino-2,3,4,5-tetrahydro-1-benzoxepin-5-ol were obtained as a residue. According to HPLC analysis (see Example 1A) this mixture contained in addition to 74.3 percent of the p-toluenesulfonic acid salt of the title compound, 15.5 percent of the corresponding 3,5-trans epimer compound.

(B) Isolation of the cis epimer:
The mixture of p-toluenesulfonic acid salts obtained as described above was dissolved in 200 ml isopropanol, and the solution was reduced in volume until the onset of crystallization and cooled. After the cooling, the crystals which formed were removed by filtration and once again recrystallized from isopropanol in the above-described manner. Pure 3,5-cis-3-methylamino-2,3,4,5-tetrahydro-1-benzoxepin-5-ol-p-toluenesulfonate was obtained having a melting point of 163 degrees C.

If desired, the title compound and its hydrochloride can be obtained from the mixture of p-toluenesulfonic acid salts obtained in Example 2A analagous to the methods described in Examples 1B2 and 1B3.

EXAMPLE 3

3,5-cis-3-methylamino-2,3,4,5-tetrahydro-1-benzoxepin-5-ol (A) 19 g 3-methylamino-1-benzoxepin-5(2H)-one were suspended in 130 ml methanol, and gaseous hydrogen chloride was introduced into the suspension with stirring in order to convert it into its hydrochloride. The amine thereby goes into solution with warming. Subsequently approximately 40 ml methanol were distilled from the solution. The solution was allowed to stand to crystallize the hydrochloride which was formed, and the crystals which formed were removed by filtration. 22 g 3-methylamino-1-benzoxepin-5(2H)-one hydrochloride were obtained which were used without further purification in the following hydrogenation.

(B) 22 g 3-methylamino-1-benzoxepin-5(2H)-one hydrochloride were hydrogenated for a period of 3.5 hours under a hydrogen pressure of 50 bar at 40 degrees C. in the presence of 0.2 g Adams Catalyst in 150 ml methanol, and the reaction mixture was worked up as described in Example 1A. The hydrogenation product obtained as a residue contains, according to HPLC analysis as described in Example 1A, 77.1 percent of the hydrochloride of the title compound besides 18.2 percent of the corresponding 3,5-trans compound.

The title compound (melting point 100–103 degrees C.) and its hydrochloride (melting point 190 degrees C.) can be obtained from the mixture as described in Example 1B.

EXAMPLE 4

3,5-cis-3-methylamino-2,3,4,5-tetrahydro-1-benzoxepin-5-ol 3,5-cis-3-methylamino-2,3,4,5-tetrahydro-1-benzoxepin-5-ol was obtained analagous to the methods described in Examples 1A, 2A and 3A+B by hydrogenation of 3-methylamino-1-benzoxepin-5(2H)-one in the presence of Adams Catalyst under the reaction conditions listed in the following table. In addition to the reaction conditions, the table lists the total yields of 3-methylamino-2,3,4,5-tetrahydro-1-benzoxepin-5-ols as well as the ratio of 3,5-cis to 3,5-trans compounds in the hydrogenation product as determined by HPLC according to the method given in Example 1A.

TABLE 1

| Example No. | Starting Material** | Added Acid*** (equivalents*) | Solvent (ml*) | $PtO_2$ Amount g* | $H_2$ Pressure bar | Reaction Temp. °C. | Reaction Time hours | Total Yield % | Cis/trans % |
|---|---|---|---|---|---|---|---|---|---|
| 4a | Ba | HCl (0.95) | $CH_3OH$ (3024) | 2.46 | 100 | 40 | 2.5 | 78 | 80/20 |
| 4b | Ba | HCl (1.05) | $CH_3OH$ (3024) | 2.46 | 100 | 40 | 2.5 | 79 | 79/21 |
| 4c | Cl | — | $CH_3OH$ (2800) | 16 | 6 | 50 | 2.5 | 81 | 72/28 |
| 4d | Su | — | $CH_3OH$ (2800) | 16 | 6 | 50 | 2.5 | 81 | 80/20 |
| 4e | Ph | — | $CH_3OH$ (2800) | 16 | 6 | 50 | 2.5 | 80 | 81/19 |
| 4f | Ba | Cyc (1.00) | $CH_3OH$ (3024) | 2.46 | 50 | 50 | 2.5 | 83 | 77/23 |
| 4g | Ba | Oxa (1.00) | $CH_3OH$ | 16 | 6 | 50 | 2.5 | 85 | 82/18 |

TABLE 1-continued

| Example No. | Starting Material** | Added Acid*** (equivalents*) | Solvent (ml*) | PtO$_2$ Amount g* | H$_2$ Pressure bar | Reaction Temp. °C. | Reaction Time hours | Total Yield % | Cis/trans % |
|---|---|---|---|---|---|---|---|---|---|
| | | | (2800) | | | | | | |

*per 1 mole of 3-methylamino-1-benzoxepin-5 (2H)—one
**Cl = hydrochloride, Su = sulfate, Ph = phosphate, Ba = base
***HCl = hydrogen chloride, Cyc = cyclohexylaminosulfonic acid, Oxa = acid

EXAMPLE 5

3,5-cis-7-chloro-3-methylamino-2,3,4,5-tetrahydro-1-benzoxepin-5-ol

The title compound was obtained by hydrogenation of 7-chloro-3-methylamino-1-benzoxepin-5(2H)-one with hydrogen according to the method described in Example 3A+B. The hydrogenation took place at ambient temperature and at a hydrogen pressure of 100 bar. The reaction time was 4 hours. The ratio of 3,5-cis compound to 3,5-trans compound in the hydrogenation product (total yield of 7-chloro-3-methylamino-2,3,4,5-tetrahydro-1-benzoxepin-5-ol hydrochlorides=73 percent) amounted to 88:12 according to HPLC analysis (see Example 1A). The hydrochloride of the title compound was recovered from the resulting mixture according to the method described in Example 1B1, melting point: 172–173 degrees C.

EXAMPLE 6

3,5-cis-3-ethylamino-2,3,4,5-tetrahydro-1-benzoxepin-5-ol

The title compound was produced by hydrogenation of 3-ethylamino-1-benzoxepin-5(2H)-one with hydrogen according to the method described in Example 3A+B. The hydrogenation took place at 50 degrees C. and at a hydrogen pressure of 6 bar. The reaction time was 2.5 hours. The ratio of 3,5-cis compound to 3,5-trans compound in the hydrogenation product (total yield of 3-ethylamino-2,3,4,5-tetrahydro-1-benzoxepin-5-ol hydrochlorides=79 percent) amounted to 79:21 according to HPLC analysis (see Example 1A).

The cyclohexyl sulfonate of the title compound was obtained from the resulting mixture analagous to the method described in Example 1B2, melting point: 150 degrees C.

EXAMPLE 7

3,5-cis-7-methyl-3-methylamino-2,3,4,5-tetrahydro-1-benzoxepin-5-ol

The title compound was obtained by hydrogenation of 7-methyl-3-methylamino-1-benzoxepin-5(2H)-one with hydrogen according to the method described in Example 3A+B. The hydrogenation took place at a temperature of 50 degrees C. and a hydrogen pressure of 6 bar. The reaction time amounted to 2.5 hours. In the hydrogenation product (total yield of 7-methyl-3-methylamino-2,3,4,5-tetrahydro-1-benzoxepin-5-ol hydrochlorides=76 percent) the ratio of 3,5-cis compound to 3,5-trans compound amounted to 78:22 according to HPLC analysis (see Example 1A). The hydrochloride of the title compound was recovered from the resulting mixture according to the method described in Example 1B1; melting point: 199–200 degrees C.

EXAMPLE 8

3,5-cis-3-methylamino-2,3,4,5-tetrahydro-1-benzoxepin-5-ol 80 ml of acetic acid were added to a mixture of 189 g 3-methylamino-1-benzoxepin-5(2H)-one and 174 g borane/tert.butylamine complex in 500 ml toluene, and the reaction mixture was stirred for 45 minutes. The temperature climbed to 36 degrees C. Subsequently 100 ml acetic acid were added dropwise over a period of 30 minutes. The temperature climbed to 60 degrees C. The reaction mixture was cooled to 50 degrees C. and stirred for a further 30 minutes. Thereafter a further 60 ml of acetic acid were added, and the temperature was held at 50–60 degrees C. for two more hours by heating. Without prior cooling the reaction mixture was stirred into a mixture of 1000 g crushed ice and 250 ml concentrated hydrochloric acid in such a way that the temperature did not rise above 25 degrees C. The organic phase was separated and washed three times with 90 ml water and 10 ml concentrated hydrochloric acid each time. The aqueous phase was rendered alkaline by addition of 540 ml concentrated ammonia and extracted three times with 500 ml methylene chloride each time and four times with 200 ml methylene chloride each time. The combined methylene chloride phases were dried over sodium sulfate, filtered and the solvent was distilled off under reduced pressure. 183 g of raw product were obtained which comprised a mixture of 3,5-cis-3-methylamino-2,3,4,5-tetrahydro-1-benzoxepin-5-ol and the corresponding 3,5-trans compound. According to HPLC analysis by the method described in Example 1A, the mixture contained 81.8 percent 3,5-cis-3-methylamino-2,3,4,5-tetrahydro-1-benzoxepin-5-ol and 18.2 percent of the corresponding 3,5-trans compound. The title compound (melting point: 100–103 degrees C.) or its hydrochloride (melting point: 190 degrees C.) was obtained from this mixture by methods analagous to those described in Examples 1B1 and 1B2.

EXAMPLE 9

3,5-cis-3-methylamino-2,3,4,5-tetrahydro-1-benzoxepin-5-ol

The title compound was obtained by reduction of 3-methylamino-1-benzoxepin-5(2H)-one with a borane/amine complex by methods analagous to those described in Example 8 under the reaction conditions listed in the following Table II. Besides the reaction conditions, the total yields of 3-methylamino-2,3,4,5-tetrahydro-1-benzoxepin-5-ols as well as the ratio of 3,5-cis compound to 3,5-trans compound, determined by HPLC according to the method described in Example 1A, are given in the table.

TABLE II

| Example No. | Amine Component | BH₃—Amine Complex Complex Amount moles* | Solvent Mixture** Aprotic Solvent/Acid proportions by volume | | Reaction Temp. °C. | Reaction Time hours | Total Yield % | Cis/trans % |
|---|---|---|---|---|---|---|---|---|
| 8a | HN(CH₃)₂ | 2 | Tol/Acet | (50:24) | 60 | 4 | 85 | 65/35 |
| 8b | H₂N—C(CH₃)₃ | 2 | Tol/Acet | (20:3) | RT*** | 50 | 80 | 85/15 |
| 8c | H₂N—C(CH₃)₃ | 2 | CH₂Cl₂/Acet | (20:2.4) | RT*** | 48 | 90 | 90/10 |
| 8d | H₂N—C(CH₃)₃ | 2 | Tol/Acet | (20:2.4) | 45 | 3 | 90 | 88/12 |
| 8e | H₂N—C(CH₃)₃ | 2 | CH₂Cl₂/Acet | (20:2.4) | 45 | 6 | 89 | 89/11 |
| 8f | H₂N—C(CH₃)₃ | 3 | Tol | | 100 | 48 | 65 | 64/36 |

*per 1 mole of 3-methylamino-1-benzoxepin-5 (2H)—one
**Tol = toluene, CH₂Cl₂ = methylene chloride, Acet —glacial acetic acid
***RT = room temperature

EXAMPLE 10

3,5-cis-7-chloro-3-methylamino-2,3,4,5-tetrahydro-1-benzoxepin-5-ol

The title compound was obtained by reduction of 7-chloro-3-methylamino-1-benzoxepin-5(2H)-one with borane/tert.butylamine according to the method described in Example 8. According to HPLC analysis by the method described in Example 1A, the ratio of 3,5-cis compound to 3,5-trans compound in the reduction product amounted to 98.2 (total yield of 7-chloro-3-methylamino-2,3,4,5-tetrahydro-1-benzoxepin-5-ols=70 percent). The hydrochloride of the title compound was obtained from the resulting mixture according to the method described in Example 1B2; melting point: 172–173 degrees C.

EXAMPLE 11

3,5-cis-3-diethylamino-2,3,4,5-tetrahydro-1-benzoxepin-5-ol

The title compound was produced by reduction of 3-diethylamino-1-benzoxepin-5(2H)-one with borane/tert.butylamine according to the method described in Example 8. In the reduction product (total yield of 3-diethylamino-2,3,4,5-tetrahydro-1-benzoxepin-5-ols=91 percent) the ratio of 3,5-cis compound to 3,5-trans compound amounted to 67:33 according to HPLC analysis by the method described in Example 1A. The p-toluenesulfonate of the title compound was obtained from the resulting mixture analagous to the method described in Example 1B2; melting point: 185–187 degrees C.

EXAMPLE 12

3,5-cis-7-methyl-3-methylamino-2,3,4,5-tetrahydro-1-benzoxepin-5-ol

The title compound was obtained by reduction of 7-methyl-3-methylamino-1-benzoxepin-5(2H)-one with borane/tert.butylamine according to the method described in Example 8. The ratio of 3,5-cis compound to 3,5-trans compound in the reduction product (total yield of 7-methyl-3-methylamino-2,3,4,5-tetrahydro-1-benzoxepin-5-ols=73 percent) amounted to 96:4 according to HPLC analysis by the method described in Example 1A. The hydrochloride of the title compound was obtained from the resulting mixture by the method described in Example 1B2; melting point: 199–200 degrees C.

The foregoing description has been set forth merely to illustrate the invention and is not intended to be limiting. Since modifications of the described embodiments incorporating the spirit and substance of the invention may occur to persons skilled in the art, the scope of the invention is to be limited solely with respect to the appended claims and equivalents.

We claim:

1. A process for producing cis-2,3,4,5-tetrahydro-3-amino-1-benzoxepin-5-ols corresponding to the Formula I:

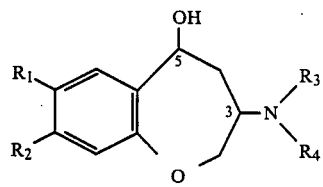

wherein the substituents in the 3- and 5-positions are cis to each other, and
R₁ represents hydrogen, halogen, or alkyl having 1–4 carbon atoms,
R₂ represents hydrogen, halogen, or alkyl having 1–4 carbon atoms,
R₃ represents hydrogen or alkyl having 1–5 carbon atoms, and
R₄ represents hydrogen,
and their acid addition salts, wherein
a 3-amino-1-benzoxepin-5(2H)-one corresponding to the Formula II

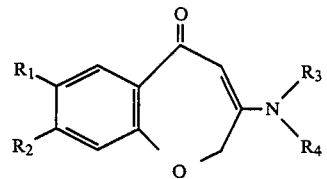

wherein R₁, R₂, R₃ and R₄ have the above meanings is diastereoselectively reduced to a mixture of 2,3,4,5-tetrahydro-3-amino-1-benzoxepin-5-ols containing a predominant portion of cis-compounds corresponding to Formula I by reducing a compound corresponding to Formula IIa

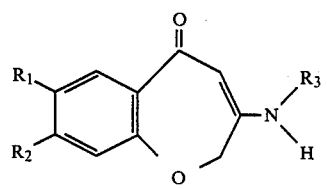

wherein $R_1$, $R_2$ and $R_3$ have the above meanings, with hydrogen in the presence of a platinum oxide catalyst in a protic, polar, organic solvent in the presence of an equivalent amount of an acid which is stable under the reaction conditions, and isolating the cis-2,3,4,5-tetrahydro-3-amino-1-benzoxepin-5-ol from the resulting reaction product.

2. A process according to claim 1, wherein the cis-2,3,4,5-tetrahydro-3-amino-1-benzoxepin-5-ol is isolated in the form of an acid addition salt, further comprising the step of converting the acid addition salt to a free base.

3. A process according to claim 1, wherein the cis-2,3,4,5-tetrahydro-3-amino-1-benzoxepin-5-ol is isolated in the form of a free base, further comprising the step of converting the free base to an acid addition salt.

4. A process according to claim 1, wherein the compound corresponding to Formula II or Formula IIa is 3-methylamino-1-benzoxepin-5(2H)-one.

5. A process according to claim 1, wherein the acid is selected from the group consisting of hydrogen halide acids, unsubstituted benzene sulfonic acids, and benzene sulfonic acids in which the benzene ring is substituted by lower alkyl or halogen.

6. A process according to claim 1, wherein the compound of Formula IIa is reacted with an acid to form an acid addition salt containing one equivalent of acid, and the resulting acid addition salt is subjected to hydrogenation.

7. A process according to claim 6, wherein the acid is hydrochloric acid.

8. A process according to claim 5, wherein the compound of Formula IIa is reacted with an acid to form an acid addition salt containing one equivalent of acid, and the resulting acid addition salt is subjected to hydrogenation.

9. A process according to claim 8, wherein the acid is hydrochloric acid.

10. A process according to claim 5, wherein the hydrogenation is carried out in the presence of from 2 to 5 g of platinum oxide catalyst per mole of compound of Formula IIa at a hydrogen pressure of from 40 to 60 bar in a lower alcohol.

* * * * *